United States Patent [19]

Albrecht et al.

[11] 4,400,196
[45] Aug. 23, 1983

[54] HERBICIDAL COMPOSITIONS

[75] Inventors: Konrad Albrecht, Kelkheim; Peter Langelüddeke, Hofheim am Taunus, both of Fed. Rep. of Germany

[73] Assignee: Hoechst Aktiengesellschaft, Frankfurt am Main, Fed. Rep. of Germany

[21] Appl. No.: 303,373

[22] Filed: Sep. 18, 1981

[30] Foreign Application Priority Data

Sep. 20, 1980 [DE] Fed. Rep. of Germany ....... 3035554

[51] Int. Cl.³ .......................................... A01N 57/00
[52] U.S. Cl. .................................... 71/86; 71/DIG. 1
[58] Field of Search .............................. 71/86, DIG. 1

[56] References Cited

U.S. PATENT DOCUMENTS

| | | | |
|---|---|---|---|
| 4,120,688 | 10/1978 | Otten | 71/86 |
| 4,159,901 | 7/1979 | Beestman et al. | 71/86 |
| 4,168,639 | 9/1979 | Rupp et al. | 71/86 |
| 4,205,977 | 6/1980 | Dingwall et al. | 71/86 |
| 4,226,610 | 10/1980 | Takematsu et al. | 71/86 |
| 4,265,654 | 5/1981 | Takematsu et al. | 71/120 |
| 4,311,512 | 1/1982 | Schwartz | 71/67 |

Primary Examiner—Glennon H. Hollrah
Attorney, Agent, or Firm—Curtis, Morris & Safford

[57] ABSTRACT

Herbicidal agents, containing a compound of the formula

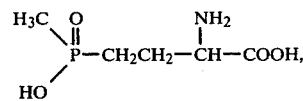

the lower alkyl ester thereof or the salts thereof with acids or bases as the active ingredient (I) and coconut fatty alkyl-benzyldimethylammoniumchloride (II) or the alkali metal salt or ammonium salt of a ($C_{12}$–$C_{16}$) alcohol polyglycol ether sulfate (III) as an additive, exhibit an increased herbicidal activity compared to active ingredient preparations which do not contain the additives (II) or (III), and, in addition, can form stable aqueous solutions.

9 Claims, No Drawings

HERBICIDAL COMPOSITIONS

It is already known from U.S. Pat. No. 4,168,963 that compounds of the formula I

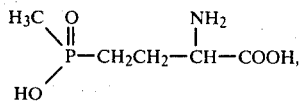

and their derivatives have a good and broad activity against weeds of many botanical families. They are therefore suitable for non-selectively combating undesired plant growth, for example on agricultural cultivated areas, or in industrial sites and railway lines, and for use in fruit cultivation and in viticulture.

Furthermore, it is known that the activity of herbicides can be improved in many cases by the addition of surface-active agents (see German Offenlegungsschrift Nos. 2,725,823 and 2,554,532). $C_{12}-C_{18}$ fatty alcohol polyglycol ethers or alkylphenol polyglycol ethers are particularly frequently used for this purpose. The addition of surface-active agents of this type also leads to an increase in action for the compounds of the formula I. However, formulation problems occur in this process, which make it impossible to render this desired effect useful in practice.

Owing to their solubility in water, compounds of the formula I are preferably formulated and applied as aqueous solutions. However, the solubility in water decreases greatly as the temperature decreases. The active ingredients already crystallise out from aqueous solution at temperatures of about 0° C. The formulations thus no longer conform to the stability specifications of CIPAC and WHO, which require, inter alia, that it be possible to store, manipulate and apply active ingredient solutions even on the incidence of frost, and provide for stability tests even at −10° C.

The solubility can be improved by the addition of small quantities of polar organic solvents, such as dioxan, dimethylformamide (DMF), dimethylsulfoxide (DMSO) or methyl glycol. However, when many surface-active agents which are customarily used in formulations of plant protecting agents, for example fatty alcohol polyglycol ethers, such as isotridecyl alcohol polyglycol ether, dodecyl alcohol polyglycol ether and ($C_{12}-C_{18}$)-alcohol polyglycol ether, and also, for example, sodium lauryl sulfate, the sodium salt of the isodecylsulfursuccinic acid half ester, sodium oleoyl-N-methyltauride or sodium lauryl polyglycol ether phosphate, are added to aqueous or aqueous/organic solutions of compounds of formula I or derivatives thereof, a phase separation occurs, so that the surface-active additive is salted out by the active ingredient. This leads to cloudiness and to solid or liquid deposits. Apart from any properties which increase action, the surface-active agents mentioned are thus unsuitable, in principle, for the preparation of stable formulations of active ingredients of the formula I or derivatives thereof.

Although another group of surface-active agents—for example alkylphenol polyglycol ether, quaternary ammonium salts and condensation products of fatty amines with ethylene oxide—are not salted out, they have to be added in considerable quantities. To achieve a significant increase in action, at least 2-3 parts of these agents are required relative to 1 part of active ingredient. As a consequence of this, the active ingredient content in formulations of this type is relatively small. Liquid active ingredient concentrates which are stable to cold and which have a maximum active ingredient content of 10%, in addition to 20–30% of the surface-active agent, can be obtained in this manner. About 10 liters per hectare of concentrates of this type are required (appropriately diluted with water) to achieve the desired herbicidal action. This is contrary to the requirement for preparing active ingredient concentrates with as high a proportion of active ingredient as possible, in order to save transport costs and packing material.

Therefore, liquid formulations of the compounds of formula I are required to exhibit the following:

(1) The formulations must be stable to cold
(2) The formulations should have as high a concentration as possible of active ingredient
(3) The proportion of surface-active agents should be as low as possible, but simultaneously increase the herbicidal action.

These three requirements cannot be satisfied by conventional agents. However, it has surprisingly been found that the addition of comparatively small quantities of coconut fatty alkyl-benzyldimethylammonium chloride (Trade Name ®Dodigen) or alkali metal salts or ammonium salts of ($C_{12}-C_{16}$) alcohol polyglycol ether sulfates (Trade Name ®Genapol LRO) very significantly improves the herbicidal activity of (comparatively) highly concentrated aqueous or aqueous/organic solutions of compounds of the formula I or derivatives thereof, without adversely affecting their stability to cold.

The invention thus relates to herbicidal compositions containing a compound of the formula I, lower alkyl esters thereof or salts with acids or bases, in combination with coconut fatty alkyl-benzyldimethylammonium chloride (II) or an alkali metal salt or ammonium salt of a ($C_{12}-C_{16}$) alcohol polyglycol ether sulfate (III).

By the addition of these agents, it is possible to obtain stable aqueous formulations which have proportions of active ingredient of 30% and which have an increased herbicidal activity compared to active ingredient solutions which are free of additives.

The additives mentioned have the further advantage that they are solid or semi-solid and can thus be processed to give water-soluble powder formulations or granule formulations which are capable of being stored and in which the active ingredient content can be up to 50%. In contrast, the ethylene oxide condensates of fatty amines, alkylphenols and alcohols, which are customarily used as formulation auxiliaries, are, in their degrees of condensation in which they impart an improved action to the active compounds, liquid and can therefore only be worked into powder formulations after previous adsorption onto highly adsorptive insoluble silicic acids. When such formulations are used, blockage of nozzles can occur in the spraying equipment.

In contrast, powder formulations and granules containing the active ingredient can be prepared with the particularly active additives described, which formulations are water soluble and therefore completely unproblematical in use.

The compositions according to the invention contain per active ingredient unit 10–30 percent by weight, in dissolved form, or 20–50 percent by weight, in solid form of an active ingredient and 0.5-3 parts of one of the additives (II) or (III) mentioned above. In addition, further surface-active agents for improving the wetting capacity, and adhesives and binding-agents as well as de-foaming agents can be present. Solutions contain, in addition to water, one of the abovementioned polar organic solvents with boiling points preferably ≧100° C. to improve the solubility of the active ingredient.

Among the additives used according to the invention, the alkali metal salts or ammonium salts of ($C_{12}$–$C_{16}$) alcohol polyglycol ether sulfates are particularly preferred, owing to their good tolerance by warm-blooded animals and their small phytotoxic activity. They preferably contain 2–6 ethylene oxide (EO) units, and are used as such predominantly as bath additives. They have not hitherto been used in plant protection. Their formula is:

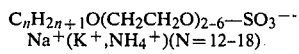
$Na^+(K^+,NH_4^+)(N=12-18)$

Aqueous solutions which contain these additives can take up particularly high proportions of active ingredient, without resulting in phase separation under cold conditions.

Coconut fatty alkyl-benzyldimethylammonium chloride, which is likewise very suitable, is a quaternary ammonium salt, the coconut fatty alkyl portion of which is obtained from coconut fatty acids. The latter is a mixture of higher saturated and unsaturated paraffinic acids with carbon numbers of (essentially) 10–18, a mixture of capric acid, lauric acid, myristic acid, palmitic acid, stearic acid and oleic acid, inter alia.

The agents according to the invention are present as solutions, water-soluble powders, wettable powders or granules, and are applied after dilution or after being dissolved in water. The following compounds, which are described in U.S. Pat. No. 4,168,963 or which can be correspondingly prepared, are particularly suitable as active ingredients: (3-Amino-3-carboxypropyl)-methylphosphinic acid(phosphinothricine; formula I), the hydrochloride thereof, monosodium, disodium, monopotassium, dipotassium, monocalcium, ammonium, $CH_3^+NH_3-$, $(CH_3)_2^+NH_2-$, $(CH_3)_3^+NH-$, $-(CH_3)_2^+NHCH_2CH_2OH$ or $-CH_3^+NH_2CH_2CH_2-OH-$ salts or methyl, ethyl, propyl or butyl esters thereof.

(In the case of the monosalts and esters of the compound of the formula I, the salt-ester formation takes place at the carboxyl group in each case).

To prepare the solutions according to the invention, the active ingredient is dissolved in a mixture composed of one part of high-boiling (b.p.=100° C.), water-miscible organic solvent and 1–2 parts of water, and the calculated quantity of the surface-active agent which increases the action, and also, if appropriate, further customary auxiliaries, such as de-foaming agents, further wetting agents or dyestuffs, are added.

Water-soluble granules are obtained by further adding water-soluble binding-agents and fillers to aqueous active ingredient solutions which contain the surface-active additives according to the invention, and subjecting the solutions obtained to a spray drying process. Water-soluble, partially hydrolyzed polyvinyl acetates, cellulose derivatives, alginates, plant gums and lignin sulfonates are examples of suitable binding-agents. Water-soluble inorganic salts which are plant-physiologically acceptable, sugar or urea can be employed as fillers.

EXAMPLES

EXAMPLE 1

Preparation of a 20% strength active ingredient powder 20 parts by weight of active ingredient, 30 parts by weight of sodium ($C_{12}$–$C_{16}$) alcohol polyglycol ether sulfate and 50 parts by weight of sodium sulfate are dissolved in 250 parts by weight of water, whilst stirring, and this active ingredient solution is dried to give a powder, by spraying at 5 to 10 atmospheres by means of a one-material nozzle in a drying tower, dry air of 130° C. being employed.

EXAMPLE 2

Preparation of a 50% strength active ingredient powder 50 parts by weight of active ingredient and 50 parts by weight of Na ($C_{12}$–$C_{16}$) alcohol polyglycol ether sulfate are dissolved in 250 parts by weight of water, and the active ingredient solution is dried as above.

EXAMPLE 3

Preparation of 30% strength active ingredient granules 30 parts by weight of active ingredient, 30 parts by weight of Na ($C_{12}$–$C_{16}$) alcohol polyglycol ether sulfate, 15 parts by weight of sodium ligninsulfonate, 5 parts by weight of partially hydrolyzed water-soluble polyvinyl acetate and 20 parts by weight of potassium chloride are dissolved in 150 parts by weight of water, and this solution is subjected, by the addition of the partially hydrolyzed polyvinyl acetate viscous solution, to a spray drying process by means of a whirler disc (circumferential velocity of the disc 80 to 100 m/second) in a drying tower, at air inlet temperatures of 190° C. and exit temperatures of 80° C. Water-soluble active ingredient granules with diameters of from 0.1 to 0.4 mm, which contain 30% by weight of active ingredient, are obtained.

Example 3

Composition and stability of various active ingredient formulations according to the invention (No. 17-24) compared with comparison formulations (No. 1-16) which have not been claimed.

TABLE 1

| Formulation No. | Active ingredient % | Water % | % organic solvent | % surface-active agent | Appearance after 14 days | | | Chemical stability after 3 months |
|---|---|---|---|---|---|---|---|---|
| | | | | | 20° C. | −10° C. | 0° C. | 50° C. |
| Comparison agent: | | | | | | | | |
| 1 | 20 | 80 | — | — | clear | cloudy | clear | stable |
| 2 | 10 | 40 | 20 DMF | 30 sodium $C_{13}$–$C_{18}$ alkanesulfonate | phase separation | | | — |

TABLE 1-continued

| Formulation No. | Active ingredient % | Water % | % organic solvent | % surface-active agent | Appearance after 14 days 20° C. | Appearance after 14 days −10° C. | Appearance after 14 days 0° C. | Chemical stability after 3 months 50° C. |
| --- | --- | --- | --- | --- | --- | --- | --- | --- |
| 3 | 10 | 40 | 30 dioxane | 20 sodium dodecylbenzenesulfonate | clear crystals | | | stable |
| 4 | 10 | 40 | 30 dioxane | 30 isodecyl alcohol polyglycol ether (6 EO) | phase separation | | | — |
| 5 | 10 | 40 | 20 dioxane | 30 isodecyl alcohol polyglycol ether (8 EO) | phase separation | | | — |
| 6 | 10 | 40 | 20 dioxane | 30 sodium dodecylsulfate | phase separation | | | — |
| 7 | 10 | 40 | 20 dioxane | 30 dodecyl alcohol polyglycol ether (10 EO) | phase separation and crystals | | | — |
| 8 | 10 | 40 | 20 dioxane | 30 sodium lauryl polyglycol ether phosphate | clear | cloudy | cloudy | stable |
| 9 | 10 | 50 | 20 DMF | 20 sodium isodecylsulfosuccinic acid half ester | clear | a few crystals | clear | stable |
| 10 | 20 | 40 | 20 dioxane | 20 oxyethylated castor oil (40 EO) | cloudy | cloudy | cloudy | stable |
| 11 | 20 | 40 | 20 DMF | 20 polyglycol stearate (20 EO) | clear | crystals | cloudy | stable |
| 12 | 20 | 30 | 20 dioxane | 20 triisobutylphenol polyglycol ether (13 EO) | clear | cloudy | clear | stable |
| 13 | 10 | 40 | 20 DMF | 10 nonylphenol polyglycol ether (10 EO) | clear | clear | clear | stable |
| 14 | 10 | 30 | 20 DMF | 20 nonylphenol polyglycol ether (10 EO) | clear | crystals | clear | stable |
| 15 | 10 | 60 | 20 DMF | 10 nonylphenol polyglycol ether (4 EO) | clear | cloudy | cloudy | stable |
| 16 | 10 | 60 | 20 DMF | 10 nonylphenol polyglycol ether (23 EO) | clear | cloudy | clear | stable |
| Agent according to the invention: | | | | | | | | |
| 17 | 10 | 50 | 30 DMF | 10 coconut fatty alkyl-benzyl-dimethylammonium chloride | clear | clear | clear | stable |
| 18 | 10 | 30 | 30 DMF | 30 coconut fatty alkyl-benzyl-dimethylammonium chloride | clear | clear | clear | stable |
| 19 | 10 | 40 | 20 DMF | 20 coconut fatty alkyl-benzyl-dimethylammonium chloride 10 nonylphenol polyglycol ether (10 EO) | clear | clear | clear | stable |
| 20 | 10 | 60 | 20 DMF | 6 coconut fatty alkyl-benzyl-dimethylammonium chloride 4 nonylphenol polyglycol ether (10 EO) | clear | clear | clear | stable |
| 21 | 20 | 40 | 20 DMF | 20 sodium $C_{12}$-$C_{16}$—alcohol polyglycol ether sulfate | clear | viscous | clear | stable |
| 22 | 20 | 40 | 20 methyl glycol | 20 sodium $C_{12}$-$C_{16}$—alcohol polyglycol ether sulfate | clear | clear | clear | stable |
| 23 | 10 | 50 | 30 N—methyl-pyrrolidone | 10 coconut fatty alkyl-benzyl-dimethylammonium chloride | clear | clear | clear | stable |
| 24 | 10 | 50 | 30 dioxane | 10 coconut fatty alkyl-benzyl-dimethylammonium chloride | clear | clear | clear | stable |

Explanations:
DMF = dimethylformamide
Number EO = number of moles of ethylene oxide in the polyglycol ether radical The agents according to the invention can be used to a large extent for combating mono-cotyledonous and dicotyledonous weeds. In the course of numerous greenhouse experiments and field experiments it was found that the good action per se of aqueous active ingredient solutions can be considerably improved, or the same effects can be achieved according to the invention with considerably smaller active ingredient dosages, if the active ingredient formulations according to the invention are used instead. In particular, a number of perennial graminaceous weeds which are otherwise difficult to combat, such as couch grass (*Agropyron repens*), Bermuda grass (*Cynodon dactylon*), perennial cyperacae and perennial dicotyledons, can be much better combated with the agents according to the invention than with the known formulations of the active ingredients.

The quantity of agents according to the invention to be used can vary within wide limits, and is, in general, appropriately between 0.1 and 10 kg/ha of active ingredient, preferably 0.3 to 5 kg/ha, particularly 0.5 to 3 kg/ha of active ingredient.

The greenhouse experiments presented in the examples which follow were arranged according to a uniform scheme: seeds of the test plants were brought to germination and emergence in pots; after the plants had developed 2 genuine leaves, they were sprayed with aqueous dilutions of the preparation according to the invention and the comparison preparations, and the sprayed quantity was the equivalent of 300 l/ha. A few days after the treatment, the action was determined by a visual assessment and expressed in % damage. The values given are averages from each of 3 identical treatments. In order to obtain a better standard of comparison, the values of a dosage series which were obtained were evaluated graphically according to the probit process, and the dosage which is necessary to obtain an action of 95% (D 95) was determined as a standard. This value is given in addition in all the tables.

The preparation numbers relate to Table 1.

EXAMPLE 1

Various preparations were tested in an experiment on wild mustard. In this experiment, it was found that the preparation 22 according to the invention was clearly superior in action to the comparison preparations 15, 16, 10, 11 and 12.

TABLE 2

Greenhouse experiment on *Sinapis arvensis* (wild mustard)
Effect 14 days after treatment

| | Dosages in kg of active ingredient/ha Effect in % | | | | | |
|---|---|---|---|---|---|---|
| | 0.25 | 0.125 | 0.062 | 0.031 | 0.015 | D 95 |
| Comparison: | | | | | | |
| Preparation 1 | 96 | 89 | 75 | 50 | 30 | 0.2 |
| Preparation 15 | 99 | 94 | 85 | 65 | 45 | 0.125 |
| Preparation 16 | 98 | 93 | 80 | 65 | 40 | 0.15 |
| Preparation 10 | 98 | 92 | 83 | 65 | 40 | 0.15 |
| Preparation 11 | 97 | 92 | 75 | 50 | 25 | 0.16 |
| Preparation 12 | 98 | 94 | 85 | 68 | 45 | 0.13 |
| according to the invention: | | | | | | |
| Preparation 22 | 100 | 98 | 98 | 93 | 80 | 0.075 |

EXAMPLE 2

In a further greenhouse experiment on oats, it was found that the preparations 22, 19, 20, 18 and 17 according to the invention also had a significantly stronger action and required significantly smaller quantities to be used than the comparison products 1, 8, 13 and 14; preparation 22 was at the top.

TABLE 3

Greenhouse experiment on *Avena sativa* (oats)

| | Dosage in kg/ha a.i. Effect in % | | | |
|---|---|---|---|---|
| | 0.5 | 0.25 | 0.125 | D 95 |
| Comparison: | | | | |
| Preparation 1 | 50 | 20 | 10 | 2.6 |
| Preparation 8 | 65 | 45 | 20 | 2.0 |
| Preparation 14 | 80 | 65 | 20 | 0.9 |
| Preparation 13 | 75 | 55 | 20 | 1.1 |
| according to the invention: | | | | |
| Preparation 22 | 96 | 80 | 55 | 0.45 |
| Preparation 19 | 93 | 75 | 40 | 0.6 |
| Preparation 20 | 85 | 60 | 25 | 0.7 |
| Preparation 18 | 93 | 70 | 45 | 0.65 |
| Preparation 17 | 91 | 57 | 25 | 0.75 |

EXAMPLE 3

In a further supplementary experiment on oats, preparation 19 according to the invention was compared with preparation 9, and it was found that its action was considerably better.

TABLE 4

Greenhouse experiment on *Avena sativa* (oats)
Effect 14 days after treatment

| | Dosage in kg/ha a.i. Effect in % | | | | |
|---|---|---|---|---|---|
| | 1.0 | 0.5 | 0.25 | 0.125 | D 95 |
| Preparation 19 | 100 | 95 | 73 | 35 | 0.5 |
| Preparation 9 | 96 | 75 | 38 | 10 | 0.9 |

EXAMPLE 4

In a series of field experiments under various habitat conditions, the preparations 19 and 22 according to the invention were compared with the comparison preparation 1; in these experiments it was found that under all conditions the preparations 19 and 22 were significantly superior to the comparison product, and the required active ingredient dosages were, for example, more than 50% below that which was required for preparation 1.

TABLE 5

Field experiments on various plant species
Effect 2 weeks after treatment

| | kg/ha a.i. Effect in % | | | |
|---|---|---|---|---|
| | 1.2 | 0.6 | 0.3 | D 95 |
| (1) *Amaranthus hybridus* | | | | |
| Preparation 1 | 85 | 75 | 40 | 2.0 |
| Preparation 19 | 98 | 85 | 65 | 0.9 |
| Preparation 22 | 99 | 95 | 78 | 0.6 |
| (2) *Datura stramonium* | | | | |
| Preparation 1 | 99 | 95 | 80 | 0.6 |
| Preparation 19 | 100 | 98 | 88 | 0.45 |
| Preparation 22 | 99 | 98 | 95 | 0.3 |
| (3) *Oryza sativa* (young rice plants) | | | | |
| Preparation 1 | 95 | 75 | 35 | 1.2 |
| Preparation 19 | 97 | 80 | 47 | 0.9 |
| Preparation 22 | 98 | 91 | 67 | 0.8 |
| (4) *Cynodon dactylon* | | | | |
| Preparation 1 | 60 | 15 | 0 | 2.5 |
| Preparation 19 | 80 | 50 | 10 | 1.9 |
| Preparation 22 | 98 | 70 | 25 | 1.0 |
| (5) *Convolvulus arvensis* | | | | |
| Preparation 1 | 88 | 65 | 35 | 1.8 |
| Preparation 19 | 92 | 82 | 55 | 1.3 |
| Preparation 22 | 95 | 83 | 60 | 1.2 |

Literature:

BLISS, C.J.: The method of probits. Science 79, 1934, 38-39

We claim:

1. An herbicidal composition consisting essentially of an herbicidally effective amount of an active ingredient of the formula

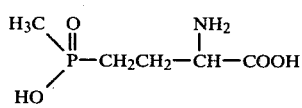

or lower alkyl esters or salts with acids or bases thereof, in combination with an effective amount of coconut fatty alkyl-benzyldimethyl-ammonium chloride or an alkali metal salt or ammonium salt of an alcohol polyglycol ether sulfate having 12 to 16 carbon atoms as surfactant.

2. The herbicidal composition of claim 1 containing, in dissolved form, 10 to 30% by weight of said active ingredient and 0.5 to 3 parts of said surfactant per part of said active ingredient.

3. The herbicidal compositionn of claim 2 further containing 15 to 35% by weight of a miscible polar organic solvent in aqueous solution selected from the group consisting of dioxane, dimethylformamide, dimethylsulfoxide, methyl glycol and N-methyl-pyrrolidone.

4. The herbicidal composition of claim 1 containing, in solid form, 20 to 50% by weight of said active ingredient, 0.5 to 3 parts of said surfactant per part of said active ingredient and an effective amount of a water-soluble binding agent selected from the group consisting of partially hydrolyzed polyvinyl acetates, cellulose derivatives, alginates, plant gums and lignin sulfonates or a water-solluble filler of an inorganic salt physiologically acceptable to plants, sugar or urea.

5. The herbicidal composition of claim 1 further containing 4 to 15% by weight of alkylphenol polyglycol ether.

6. A method for combatting weeds which comprises applying an herbicidally effective amount of the herbicidal composition defined in claim 1 to a locus of weed infestation.

7. The method of claim 6 wherein 0.1 to 10 kg/ha of said active ingredient is applied.

8. The method of claim 12 for combatting monocotyledonous and dicotyledonous weeds.

9. The method of claim 6 for combatting *Agropyron repens, Cynodon dactylon,* perennial cyperacae or perennial dicotyledons.

* * * * *